United States Patent [19]

Turnland

[11] Patent Number: 5,360,401
[45] Date of Patent: Nov. 1, 1994

[54] CATHETER FOR STENT DELIVERY

[75] Inventor: Todd H. Turnland, Mountain View; Jorito L. Fernando, Modesto, both of Calif.

[73] Assignee: Advanced Cardiovascular Systems, Inc., Santa Clara, Calif.

[21] Appl. No.: 19,046

[22] Filed: Feb. 18, 1993

[51] Int. Cl.$^5$ .................................................. A61M 29/00
[52] U.S. Cl. .................................... 604/96; 606/195
[58] Field of Search .............................. 604/96–103, 604/53, 95, 107; 606/192, 194, 195; 128/656–658

[56] References Cited

U.S. PATENT DOCUMENTS

| | | |
|---|---|---|
| 3,868,956 | 3/1975 | Alfidi et al. . |
| 4,503,569 | 3/1985 | Dotter . |
| 4,512,338 | 4/1985 | Balko et al. . |
| 4,553,545 | 11/1985 | Maass et al. . |
| 4,560,374 | 12/1985 | Hammerslag . |
| 4,655,771 | 4/1987 | Wallsten . |
| 4,665,918 | 5/1987 | Garza et al. . |
| 4,681,110 | 7/1987 | Wiktor ........................ 606/194 |
| 4,733,665 | 3/1988 | Palmaz . |
| 4,748,982 | 6/1988 | Horzewski et al. . |
| 4,760,849 | 8/1988 | Kropf . |
| 4,762,128 | 8/1988 | Rosenbluth . |
| 4,768,507 | 9/1988 | Fischell . |
| 4,771,777 | 9/1988 | Horzewski et al. . |
| 4,795,458 | 1/1989 | Regan . |
| 4,800,882 | 1/1989 | Gianturco . |
| 4,830,003 | 5/1989 | Wolff et al. . |
| 4,856,516 | 8/1989 | Hillstead . |
| 4,875,480 | 10/1989 | Imbert ........................ 606/194 |
| 4,878,906 | 11/1989 | Lindemann et al. . |
| 4,886,062 | 12/1989 | Wiktor . |
| 4,887,997 | 12/1989 | Okada . |
| 4,907,336 | 3/1990 | Gianturco . |
| 4,913,141 | 4/1990 | Hillstead . |
| 4,923,464 | 5/1990 | DiPisa, Jr. . |
| 4,950,227 | 8/1990 | Savin et al. . |
| 4,969,458 | 11/1990 | Wiktor . |
| 5,019,042 | 5/1991 | Sahota ........................ 604/101 |
| 5,019,090 | 5/1991 | Pinchuk ........................ 606/194 |
| 5,057,120 | 10/1991 | Farcot ........................ 606/194 |
| 5,059,177 | 10/1991 | Towne et al. ................ 604/96 |
| 5,061,273 | 10/1991 | Yock . |
| 5,098,412 | 3/1992 | Shiu ........................ 604/280 |
| 5,133,732 | 7/1992 | Wiktor . |
| 5,135,536 | 8/1992 | Hillstead . |
| 5,154,725 | 10/1992 | Leopold ........................ 606/194 |
| 5,156,594 | 10/1992 | Keith ........................ 604/96 |
| 5,158,548 | 10/1992 | Lau et al. ................ 604/164 X |
| 5,161,547 | 11/1992 | Tower . |
| 5,163,951 | 11/1992 | Pinchuk et al. . |
| 5,163,952 | 11/1992 | Froix . |
| 5,163,958 | 11/1992 | Pinchuk . |
| 5,171,262 | 12/1992 | MacGregor . |
| 5,183,085 | 2/1983 | Timmermans . |
| 5,192,295 | 3/1993 | Danforth et al. ........ 606/194 |
| 5,192,297 | 3/1993 | Hull . |
| 5,192,307 | 3/1993 | Wall . |
| 5,192,311 | 3/1993 | King et al. . |
| 5,195,984 | 3/1993 | Schatz ........................ 606/195 |
| 5,197,978 | 3/1993 | Hess . |

FOREIGN PATENT DOCUMENTS

| | | |
|---|---|---|
| A-8901798 | 3/1989 | European Pat. Off. . |
| WO-A-8908433 | 9/1989 | European Pat. Off. . |
| A-0408245 | 1/1991 | European Pat. Off. . |
| 0416662A2 | 3/1991 | European Pat. Off. . |
| 0505686A1 | 9/1992 | European Pat. Off. . |
| A-3640745 | 6/1987 | Germany . |
| 3743139 | 7/1989 | Germany ............... 604/53 |

Primary Examiner—C. Fred Rosenbaum
Assistant Examiner—Frank Wilkens, III
Attorney, Agent, or Firm—Fulwider, Patton, Lee & Utecht

[57] ABSTRACT

A stent delivery catheter system employing a retractable protective sheath for protecting a body lumen from a stent delivered by the catheter. The catheter has a plurality of lumens, with at least one lumen devoted to housing a rod, wire or hypotube that retracts the protective sheath. The lumen housing the retracting member can carry a flushing fluid to purge the distal portion of the catheter.

18 Claims, 2 Drawing Sheets

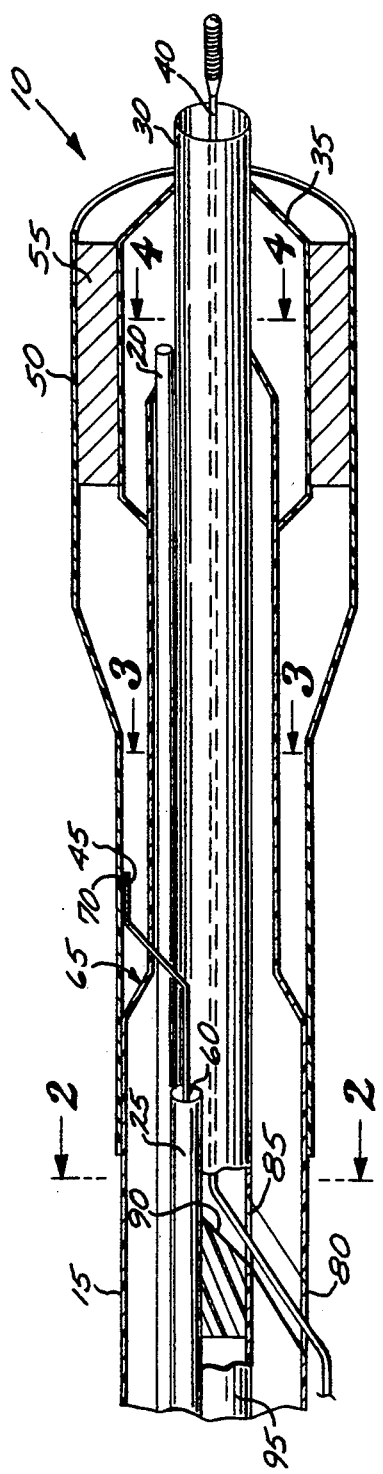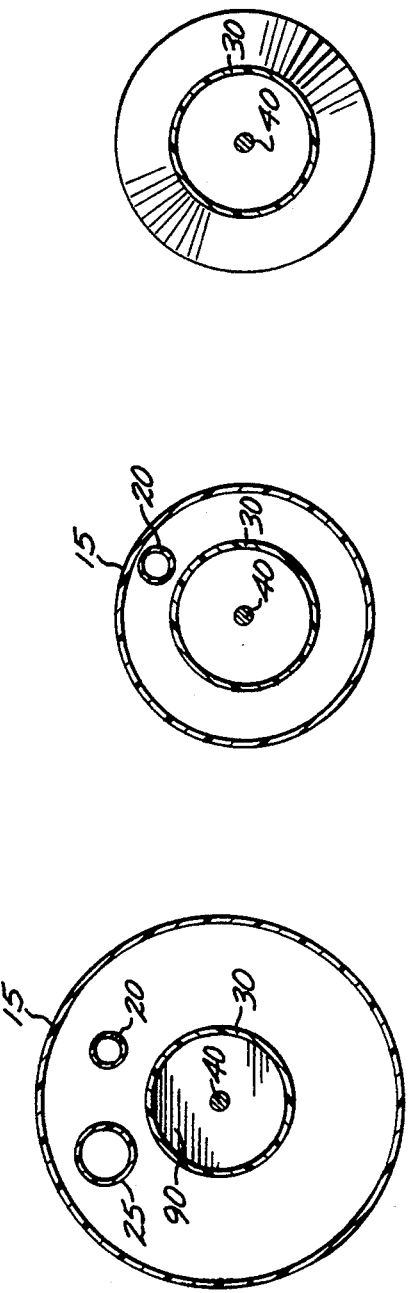

CATHETER FOR STENT DELIVERY

BACKGROUND OF THE INVENTION

Field of the Invention

The invention relates to a protective covering, membrane or sheath for a stent delivered by a balloon dilatation catheter, such as the kind used in percutaneous transluminal coronary angioplasty (PTCA) procedures.

In typical PTCA procedures, a guiding catheter is percutaneously introduced into the cardiovascular system of a patient through the brachial or femoral arteries and advanced through the arteries until the distal end is in the ostium of the desired coronary artery. A guidewire and a dilatation catheter having a balloon on the distal end are introduced through the guiding catheter with the guidewire sliding within an inner lumen of the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the preformed balloon is inflated to a predetermined size with radiopaque liquid at a relatively high pressure to compress the atherosclerotic plaque of the lesion against the inside of the artery wall and dilate the artery. The balloon is then deflated to a small profile, so that the dilatation catheter can be withdrawn from the patient's vasculature and blood flow resumed through the dilated artery.

In angioplasty procedures of the kind referenced above, there may be restenosis of the artery, which may require another angioplasty procedure or a surgical bypass operation. To help prevent abrupt closure, dissection, or restenosis, a physician can implant an intravascular prosthesis for maintaining vascular patency, called a stent, inside the artery at the lesion. The stent is expanded to a larger diameter, often by a balloon catheter. The stent is left in the artery, either temporarily or permanently, at the site of a dilated lesion.

The stent is delivered to the dilated lesion site by a catheter. The stent may have protuberances on its outer surface facing the patient's lumen wall. If such protuberances rub the lumen wall during delivery of the stent, they may damage the lumen wall and cause the stent to be displaced from the catheter.

SUMMARY OF THE INVENTION

The present invention is directed to an improved protective sheath for covering a stent delivered by a catheter adapted for PTCA use, although the present invention is in no way limited to PTCA use, as should be understood by one skilled in the art. The present invention is also directed to an improved tri-lumen catheter in an rapid-exchange (Rx) catheter design, with a lumen devoted to protecting the member devoted to retracting the protective sheath. The catheter may also be an over-the-wire or fixed wire catheter.

These and other features of the present invention are disclosed in the following description.

BRIEF DESCRIPTION OF THE DRAWINGS

FIG. 1 is an schematic axial cross-section of the distal end of the stent delivery balloon catheter of the present invention.

FIG. 2 is an axial cross-section across line 2—2 in FIG. 1.

FIG. 3 is an axial cross-section across line 3—3 in FIG. 1.

FIG. 4 is an axial cross-section across line 4—4 in FIG. 1.

Figure 5:
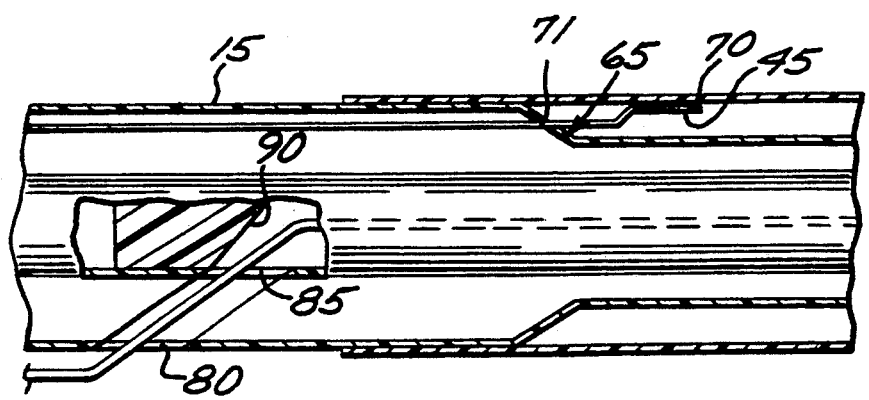
FIG. 5 is a schematic axial cross-section of the distal portion of the stent delivery balloon catheter depicting the retracting member and longitudinal slit in the outer member.

As can be appreciated by one skilled in the art, the above drawings are not necessarily to scale.

DETAILED DESCRIPTION OF THE INVENTION

As depicted in FIGS. 1-4, there is shown the distal end of a catheter 10 having a catheter outer lumen 15, and a plurality of inner lumens, lumens 20, 25 and 30 disposed inside the outer lumen 15. The inner lumens may be formed from separate lumens or as passageways of a larger lumen. The lumens may be made by extrusion, coextrusion or fusion.

Inflation lumen 20 carries inflation fluid to the balloon portion 35 of the catheter, as is known per se in the art. Guidewire lumen 30 houses the guidewire 40. Retracting member lumen 25 houses a retracting member 45 that is attached to retractable sheath 50, which protects stent 55 during transport of the stent. Retracting member 45 may be a rod, wire or hypotube, that can be made of a metal or polymeric material.

The proximal section of the catheter can be formed with a hypotube, similar to the STREAK TM catheter, marketed by Advanced Cardiovascular Systems, Inc. (ACS) of Santa Clara, Cal.

Retractable sheath 50 may be flexible or rigid, and generally protects stent 55. Further details concerning this kind of sheath and the mechanics of its withdrawal may be found in commonly assigned and copending U.S. patent application Ser. No. 07/647,464, incorporated by reference herein in its entirety.

The retracting member lumen 25 may carry flushing fluid for purging and cleaning said catheter at the distal end. If the retracting member 45 is a hypotube, the hypotube can carry the purging fluid.

Retracting member 45 exits retracting member lumen 25 at exit hole 60, and continues to the outside of catheter outer lumen 15 through slit 65, which extends along the longitudinal axis of the catheter 10. The distal end of retracting member 45 is attached to the retractable sheath 50 at attachment point 70. Though a single point of attachment is shown, more than one attachment point with a plurality of retracting members and retracting member lumens may be employed.

Figure 6:
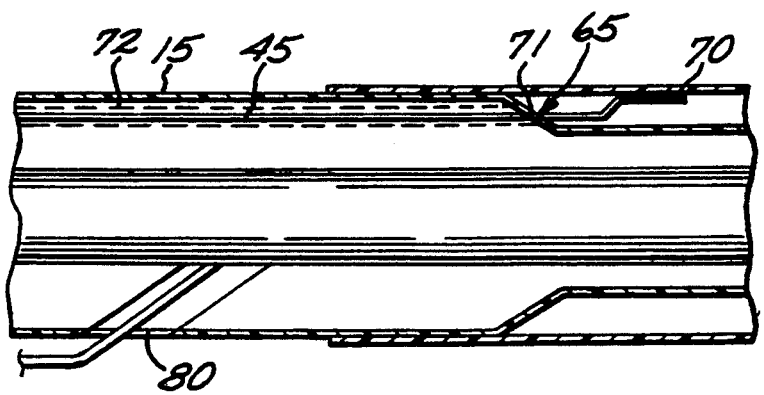
FIG. 6 is a schematic axial cross-section of a portion of the retracting member and the longitudinal slit in the catheter.

Alternatively, and as can be seen in FIGS. 5 and 6, retracting member 45 is attached to retractable sheath 50 at attachment point 70. Retractable member 45 extends through opening 71 in outer lumen 15 and is housed therein. A longitudinal slit 72 extends along outer lumen 15 and provides an exit point for retractable member 45 at a point proximal to the balloon area.

Stent 55 overlies balloon portion 35 of the catheter, and is surrounded by protective retractable sheath 50. Protective sheath 50 remains covering the underlying stent during the transportation of the stent by the balloon delivery catheter through the patient's vasculature. During the transportation of the stent protective sheath 50 protects the patient's vasculature from the stent. When it is time to expand the stent into an enlarged diameter form, to secure the stent in a patient's vasculature, sheath 50 is retracted from over stent 55.

The sheath is withdrawn from the stent by applying tension on retracting member 45 causing relative motion between sheath 50 and stent 55. Thereafter, the balloon 35 of the balloon catheter can be inflated to expand the stent from a reduced diameter to an enlarged diameter, where it remains in place in the patient's vasculature, as is known per se in the art. Retracting member 45 and its lumen 25 exit out of the proximal end of the catheter, at one branch of a two arm Luer fitting (not shown). The other arm of the Luer fitting is devoted to the inflation lumen 20. Radiopaque liquid may be pumped through inflation lumen 20. As is known per se in the art, an over-the-wire catheter may employ a three arm Luer fitting.

Any suitable material may be employed in the stent delivery catheter of the present invention, such as a catheter material that is a blend of high and low density polyethylene.

Though in the preferred embodiments above it was disclosed how the stents delivered were stents expanded by the balloon portion of the catheter, in general, the present protective sheath stent delivery catheter may deliver any type of stent. In particular, the present invention may be used with stents that are self-expanding, such as Nitinol TM material stents.

Turning attention once again to FIGS. 1-4, there are shown cut-away sections of the catheter. The figures disclose the rapid exchange feature of the catheter, which is a feature found in commonly assigned U.S. Pat. Nos. 4,748,982 and 5,061,273, incorporated herein by their entirety. As is known to those skilled in the art, the rapid exchange feature allows the guidewire to be placed outside the body of the catheter over a portion of the catheter, which facilitates the removal and exchange of catheters over the same guidewire. A plurality of radially aligned and axially coextensive slits or guidewire exit notches 80 and 85 extend over portions of the outer catheter lumen 15 and guidewire lumen 30 to allow communication between the outside of the catheter and the inside of the guidewire lumen. Guidewire 40 is thus able to traverse the outside of the catheter for a portion of the length of the catheter. A ramp 90 provides a smooth surface to the guidewire as the catheter is advanced over the guidewire. A mandrel, hypotube or stiffening rod 95 inside the guidewire lumen 30 provides increased rigidity to the portion of the catheter that is proximal to the exit notches, that is, the portion of the catheter that no longer contains the guidewire. In an over-the-wire catheter, guidewire 40 and the guidewire lumen 30 would exit through a port in a three arm Luer fitting, with the other two arms of the Luer fitting forming ports for the inflation lumen 20 and retractable member lumen 25. In a fixed wire catheter, the two arms of the Luer fitting form ports for the inflation lumen 20 and the retractable member lumen 25.

It should be understood by one skilled in the art that, while in the preferred embodiments a specialized over-the-wire balloon catheter assembly with a rapid-exchange design is employed, in general, any type of catheter may be made with the tri-lumen design disclosed herein, including any over-the-wire or fixed wire catheter assembly, or any other type of device used to expand intravascular stents. Other modifications can be made to the present invention by those skilled in the art without departing from the scope thereof.

We claim:

1. A protective sheath stent delivery catheter for delivering a stent disposed on said catheter, comprising:
    a catheter having a balloon portion;
    a protective sheath surrounding said balloon portion;
    means in operative relationship with said protective sheath for retracting said protective sheath from over said balloon portion;
    and a plurality of lumens inside said catheter, wherein at least one of said lumens houses a portion of said retracting means, and at least one other of said lumens houses a portion of a guidewire for directing said balloon portion to the site at which treatment is to be rendered.

2. The protective sheath stent delivery catheter according to claim 1, wherein:
    said retracting means is selected from the group consisting of a rod and a wire.

3. The protective sheath stent delivery catheter according to claim 2, wherein said retracting means is made from metal.

4. The protective sheath stent delivery catheter according to claim 2, wherein said retracting means is made from a polymer.

5. The protective sheath stent delivery catheter according to claim 2, wherein said retracting means is housed by a catheter outer lumen.

6. A protective sheath stent delivery catheter for delivering a stent disposed on said catheter, comprising:
    a catheter having a balloon portion;
    means for guiding said catheter to the site at which treatment is to be rendered;
    a protective sheath surrounding said balloon portion;
    means in operative relationship with said protective sheath for retracting said protective sheath from over said balloon portion; and
    said catheter having an outer lumen housing said retracting means;
    wherein said retracting means is selected from the group consisting of a rod and a wire; and
    a portion of said retracting means exits a longitudinal slit in said catheter outer lumen without said portion extending radially outwardly of said protective sheath.

7. The protective sheath stent delivery catheter according to claim 2, further comprising:
    a guidewire, and wherein said plurality of lumens include an inflation lumen for inflation of said balloon portion and a guidewire lumen for housing said guidewire.

8. The protective sheath stent delivery catheter according to claim 7, wherein said guidewire lumen has a longitudinally extending slit, and said guidewire extends through said slit and is disposed both inside said guidewire lumen and outside said guidewire lumen, to facilitate the rapid exchange of said catheter from said guidewire.

9. The protective sheath stent delivery catheter according to claim 8, wherein:
    said lumen housing said retracting means carries a fluid for purging said catheter.

10. A protective sheath stent delivery catheter for delivering a stent disposed on said catheter, comprising:
    a catheter having a balloon portion;
    a protective sheath surrounding said balloon portion;
    a guidewire; and means in operative relationship with said protective sheath for retracting said protective sheath from over said balloon portion;

at least three lumens inside said catheter, one of said lumens housing a portion of said retracting means, another of said lumens housing a portion of said guidewire, and still another of said lumens is an inflation lumen for inflating said balloon portion.

11. The protective sheath stent delivery catheter according to claim 1, wherein said catheter is a fixed wire catheter.

12. The protective stent delivery catheter according to claim 1, wherein said catheter is an over-the-wire catheter.

13. A protective sheath stent delivery catheter for delivering a stent disposed in said catheter, comprising:
a catheter having a balloon portion;
a protective sheath surrounding said balloon portion;
a retracting member in operative relationship with said protective sheath for retracting said protective sheath from over said balloon portion; and
said catheter having an outer lumen housing said retracting member; and
wherein said retracting member exits a longitudinal slit in said catheter outer lumen.

14. A protective sheath stent delivery catheter for delivering a stent disposed in said catheter comprising:
a catheter having a balloon portion;
a protective sheath surrounding said balloon portion;
a retracting member for retracting said protective sheath from over said balloon portion; and
a plurality of lumens inside said catheter, at least one said lumen housing said retracting member, said retracting member being made from a polymer.

15. A protective sheath stent delivery catheter for delivering a stent disposed in said catheter, comprising:
a catheter having a balloon portion;
a protective sheath surrounding said balloon portion;
a retracting member for retracting said protective sheath from over said balloon portion, wherein said retracting member is formed from a hypotube that carries a fluid for purging said catheter;
a plurality of lumens inside said catheter, at least one said lumen housing said retracting member; and
a guidewire, wherein said plurality of lumens includes an inflation lumen for inflation of said balloon portion and a guidewire lumen for housing said guidewire.

16. A protective sheath stent delivery catheter for delivering a stent disposed in said catheter, comprising:
a catheter having a balloon portion;
a protective sheath surrounding said balloon portion;
a retracting member for retracting said protective sheath from over said balloon portion;
a plurality of lumens inside said catheter, at least one said lumen housing said retracting member;
a guidewire, wherein said plurality of lumens include an inflation lumen for inflation of said balloon portion and a guidewire lumen for housing said guidewire; and
a longitudinally extending slit in said guidewire lumen, whereby said guidewire extends through said slit and is disposed both inside said guidewire lumen and outside said guidewire lumen to facilitate the rapid exchange of said catheter from said guidewire.

17. A protective sheath stent delivery catheter for delivering a stent disposed in said catheter, comprising:
a fixed wire catheter having a balloon portion;
a protective sheath surrounding said balloon portion;
a retracting member for retracting said protective sheath from over said balloon portion; and
a plurality of lumens inside said catheter, at least one said lumen housing said retracting member.

18. A protective sheath stent delivery catheter for delivering a stent disposed in said catheter, comprising:
a catheter having a balloon portion;
a protective sheath surrounding said balloon portion;
a retracting member for retracting said protective sheath from over said balloon portion; and
a plurality of lumens inside said catheter, including a guidewire lumen, a retracting lumen, and an inflation lumen, wherein said retracting member is housed within said retracting member lumen.

* * * * *